United States Patent [19]
Panchal et al.

[11] Patent Number: 6,062,069
[45] Date of Patent: May 16, 2000

[54] HIGH TEMPERATURE FOULING TEST UNIT

[75] Inventors: Chandrakant B. Panchal, Woodridge; Zhuoxiong Mao, Arlington Heights, both of Ill.

[73] Assignee: The University of Chicago, Chicago, Ill.

[21] Appl. No.: 09/129,689

[22] Filed: Aug. 5, 1998

[51] Int. Cl.[7] .................................................. G01N 25/00
[52] U.S. Cl. ............................... 73/53.01; 73/86; 374/7; 422/53
[58] Field of Search .............................. 73/53.01, 54.42, 73/61.46, 61.62, 61.76, 86; 374/7, 54, 139, 43; 422/53

[56] References Cited

U.S. PATENT DOCUMENTS

| | | | |
|---|---|---|---|
| 4,383,438 | 5/1983 | Eaton | 73/61.2 |
| 4,910,999 | 3/1990 | Eaton | 73/61.2 |

OTHER PUBLICATIONS

James G. Knudsen, Apparatus and Techniques for Measurement of Fouling of Heat Transfer Surfaces, p. 57–81, Mar. 1979.

"Chemical Reaction Fouling Model for Single–Phase Heat Transfer", by C.B. Panchal and A.P. Watkinson, 1993, AlChE Symposium Series No. 295, vol. 89, pp. 323–333.

"Apparatus and Techniques for Measurement of Fouling of Heat Transfer Surfaces", by J.G. Knudsen, 1981, Fouling of Heat Transfer Equipment, McGraw Hill Book Company, pp. 57–81.

"Development of an Analytical Model for Organic Fluid Fouling", by C.B. Panchal and A.P. Watkinson, ANL/ESD/TN–86, 1994, pp. 1–115.

*Primary Examiner*—Hezron Williams
*Assistant Examiner*—Thuy Vinh Tran
*Attorney, Agent, or Firm*—Mason, Kolehmainen, Rathburn & Wyss

[57] ABSTRACT

A high temperature fouling test unit is provided. The fouling test unit includes a flow tube with a fouling probe received within the flow tube. The fouling probe includes a heated section. An annular passage is defined between the fouling probe and the flow tube. An impeller is mounted within the flow tube for inducing fluid flow within the annular passage. A plurality of temperature responsive devices monitor a rate of heat transfer and a change in fluid temperature through the annular passage.

14 Claims, 7 Drawing Sheets

HIGH TEMPERATURE FOULING TEST UNIT

CONTRACTUAL ORIGIN OF THE INVENTION

The United States Government has rights in this invention pursuant to Contract No. W-31-109-ENG-38 between the United States Government and the University of Chicago.

FIELD OF THE INVENTION

The present invention relates to apparatus useful in simulating industrial fouling or corrosive conditions in process equipment, such as heat exchangers, and more particularly, relates to a high temperature fouling test unit in which flow and temperature conditions are produced in a short section of tubing to study and/or measure fouling or corrosive effects on tubing.

DESCRIPTION OF THE RELATED ART

In petroleum refineries, research laboratories, and other chemical processing operations, fouling of equipment is a major problem. Mechanisms for chemical-reaction fouling are complex and often involve several processes.

In general, insoluble foulants are formed by chemical reactions between chemical species present in the process stream. The interactive effects of the chemical reactions, fluid dynamics, and heat/mass transfer mechanisms make understanding of the fouling process quite difficult. The presence of particulate matter, inorganic salts, and incompatible species alters the overall deposition process, while the chemical reaction remains the governing process.

U.S. Pat. No. 4,383,438, issued May 17, 1983 to Paul E. Eaton discloses a fouling test apparatus. The disclosed fouling test apparatus includes a cylindrical pressure vessel, means for controlling the temperature of fluid contained in the vessel, cylindrical probe having a metallic surface concentric with the vessel walls and provided with a heater for such surface; stirrer in the form of a rotor open at least on end and positioned between and concentric with the vessel walls and the probe, and sensor for measuring the temperature of the fluid contained in the vessel and the temperature of the probe surface. The probe simulates a heat exchanger surface exposed to a fouling liquid medium. Deposits accumulate on the heated surface. The probe operates with a constant heat flux. As deposits accumulate, the surface temperature of the probe increases and is used as a measure of the deposit formation. The probe is maintained in a stationary position and the stirrer is not dependent on an electrical feed-through.

Panchal, C. B., and Watkinson, A. P., 1993, "Chemical Reaction Fouling Model for Single-Phase Heat Transfer", AIChE Symposium Series No. 295, Vol. 89, pp. 323–333, disclose a fouling model developed on the premise that the chemical reaction for generation of precursor can take place in the bulk, in the thermal-boundary layer, or at the fluid/wall interface depending upon the interactive effects of fluid dynamics, heat and mass transfer, and the controlling chemical reaction. The analysis was used to examine experimental data for fouling deposition of poly-peroxides produced by autoxidation of indene in kerosene. The effects of fluid and wall temperatures for two flow geometries were analyzed. The results showed that the relative effects of physical parameters on the fouling rate would differ for the three fouling mechanisms; therefore, it is important to identify the controlling mechanism for applying the laboratory data obtained by the closed-flow loop to industrial conditions of once through flows.

The complexity of the fouling mechanism has been the major barrier for developing effective fouling mitigation methods. Some progress has been made to develop prediction models for fouling caused by chemical reactions. However, experimental data are required for validating such prediction methods. Due to complex chemical reactions involved in the fouling process, simulation of industrial fluid dynamics and thermal conditions in a laboratory set up is quite important. Certain chemical additives are found to be ineffective to control fouling for industrial conditions, even though they were effective in a laboratory set up. Not being able to simulate the fluid dynamics and thermal conditions in the laboratory set up is believed to be the major reason. Similar observation was made to predict fouling characteristics of industrial fluids using a laboratory set up. A flow loop with circulating fluid can be used; however, such a test facility is prohibitively expensive and maintaining it free of contamination is quite difficult.

SUMMARY OF THE INVENTION

A principal object of the present invention is to provide an improved high temperature fouling test unit in which flow and temperature conditions are produced in a short section of tubing to study and/or measure fouling or corrosive effects on process equipment. Other important objects of the present invention are to provide such high temperature fouling test unit substantially without negative effects; and to provide high temperature fouling test unit that overcome some of the disadvantages of prior art arrangements.

In brief, a high temperature fouling test unit is provided. The fouling test unit includes a flow tube with a fouling probe received within the flow tube. The fouling probe includes a heated section. An annular passage is defined between the fouling probe and the flow tube. An impeller is mounted within the flow tube for inducing fluid flow within the annular passage. A plurality of temperature responsive devices monitor a rate of heat transfer and a change in fluid temperature through the annular passage.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
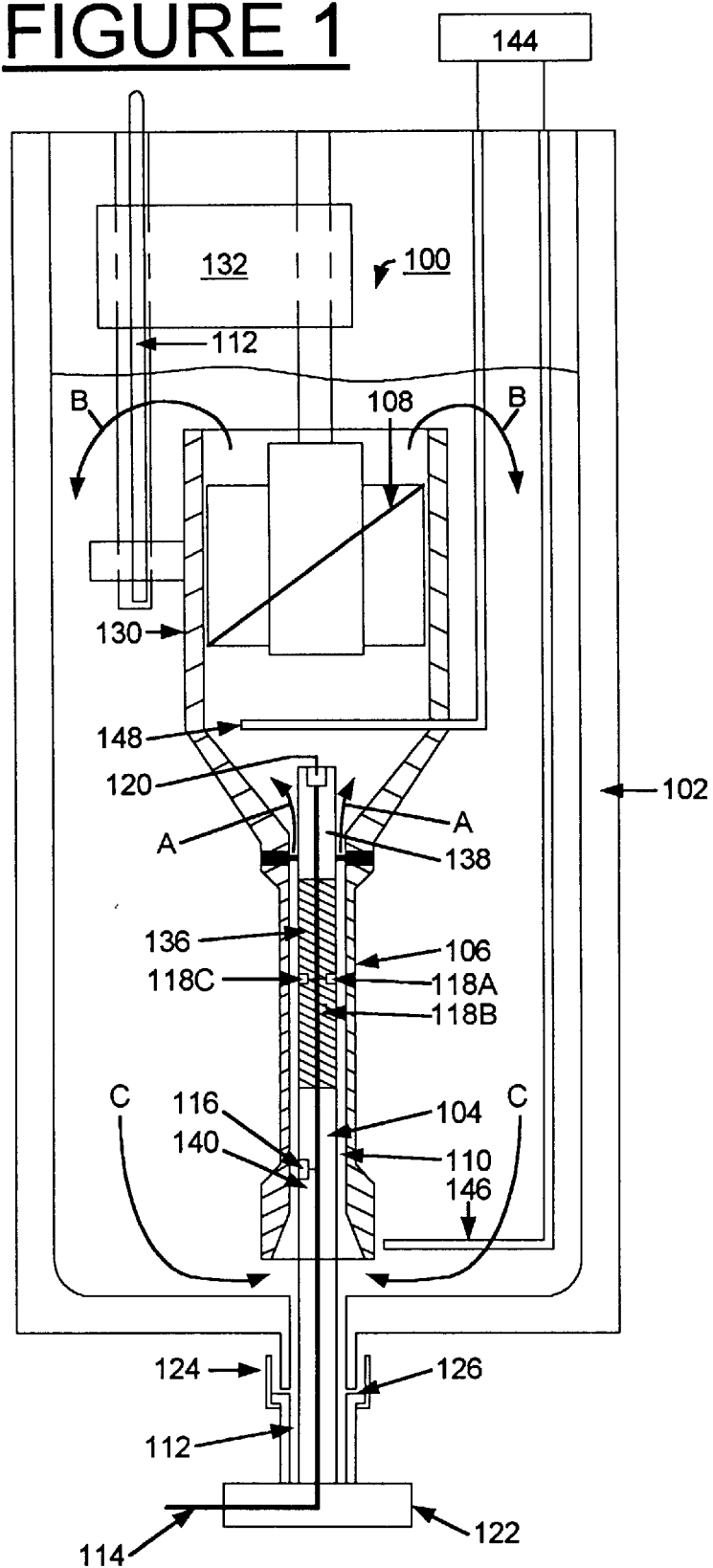
FIG. 1 is a diagrammatic view of a high temperature fouling test unit arranged in accordance with the present invention.

Having reference now to the drawings, in FIG. 1 there is illustrated a high temperature fouling test unit generally designated as 100. The new fouling test unit 100 is provided for high temperature and high-pressure fouling experiments. The fouling unit 100 not only serves as a research tool, but can be used in field testing to obtain fouling data to determine threshold fouling conditions, effectiveness of new and improved mitigation methods, and changes in the fouling characteristics due to different chemical composition and/or operating conditions. In addition to fouling experiments, the fouling unit 100 can be used for corrosion and chemical-reaction experiments.

An autoclave or high pressure vessel 102 encloses the fouling test unit 100. Among the primary components of fouling unit 100 are a fouling probe 104, a flow tube generally designated as 106 and a helical impeller generally designated as 108. The fouling probe 104 is received within the flow tube 106.

By configuring the flow tube 106 of the preferred embodiment over the probe 104, an annular passage generally designated as 110 is provided between the probe 104 and the flow tube 106. The flow tube 106 is vertically aligned and is coupled to a thermowell 112. The flow tube 106 is formed of stainless steel or similar material. Multiple wires represented generally by line 114 are connected to a plurality of thermocouples 116, 118A, 118B, 118C, and 120 and are received through a fouling probe wiring assembly 122 coupled to the fouling probe 104. A specifically arranged high temperature coupling 124 contains a gasket 126 for removably positioning the fouling probe 104.

The helical impeller 108 is located in an upper portion 130 of the flow tube 106 and is arranged for driving the fluid upwards through the tube 106 as indicated by arrows labeled A, B, and C illustrating the a fluid flow path. A mounting bracket 132 or similar structure supports the helical impeller 108 within the upper portion 130 of the flow tube 106. The interior thermocouples 116, 118A, 118B, 118C, and 120 are mounted on the fouling probe 104 or to an interior wall of the flow tube 106 within the annular passage 110. Each thermocouple 118A, 118B, 118C is positioned near the wall to monitor the rate of fouling. The thermocouples 116 and 118 measure fluid temperature entering and leaving the heated section 136, respectively. The fouling probe 104 is similar to those used by other investigators. The fouling probe 104 contains a heated section 136, an upper portion 138 and a lower portion 140. The heated section 136 of the fouling probe 104 is, for example, 76.2 mm in length. The probe 104 can easily be removed for examination and deposit sampling.

The fouling test unit 100 meets all objectives for fouling measurements including (1) low cost, (2) compact design for ease of maintenance, (3) high-temperature (>300° C.) and high-pressure (10 to 70 atm.) capabilities, and (4) known fluid dynamics. The fouling unit test 100 can be used for experiments at conditions which cover many refinery processes. Another major advantage is that fouling test unit 100 can be easily cleaned.

A differential resistance temperature device (RTD) 144 including a low temperature RTD 146 and a high temperature RTD 148 is installed across the flow tube 106 to measure the change in fluid temperature. A limitation of the fouling test unit 100 is that conventional flowmeters can not be easily installed to measure the flow rate directly inside the flow tube 106. Therefore, the flow rate is calculated on the basis of heat and mass balances. The flow rate is inversely proportional to the increase in the fluid temperature through the flow tube 106 monitored by RTD 144.

Figure 2:
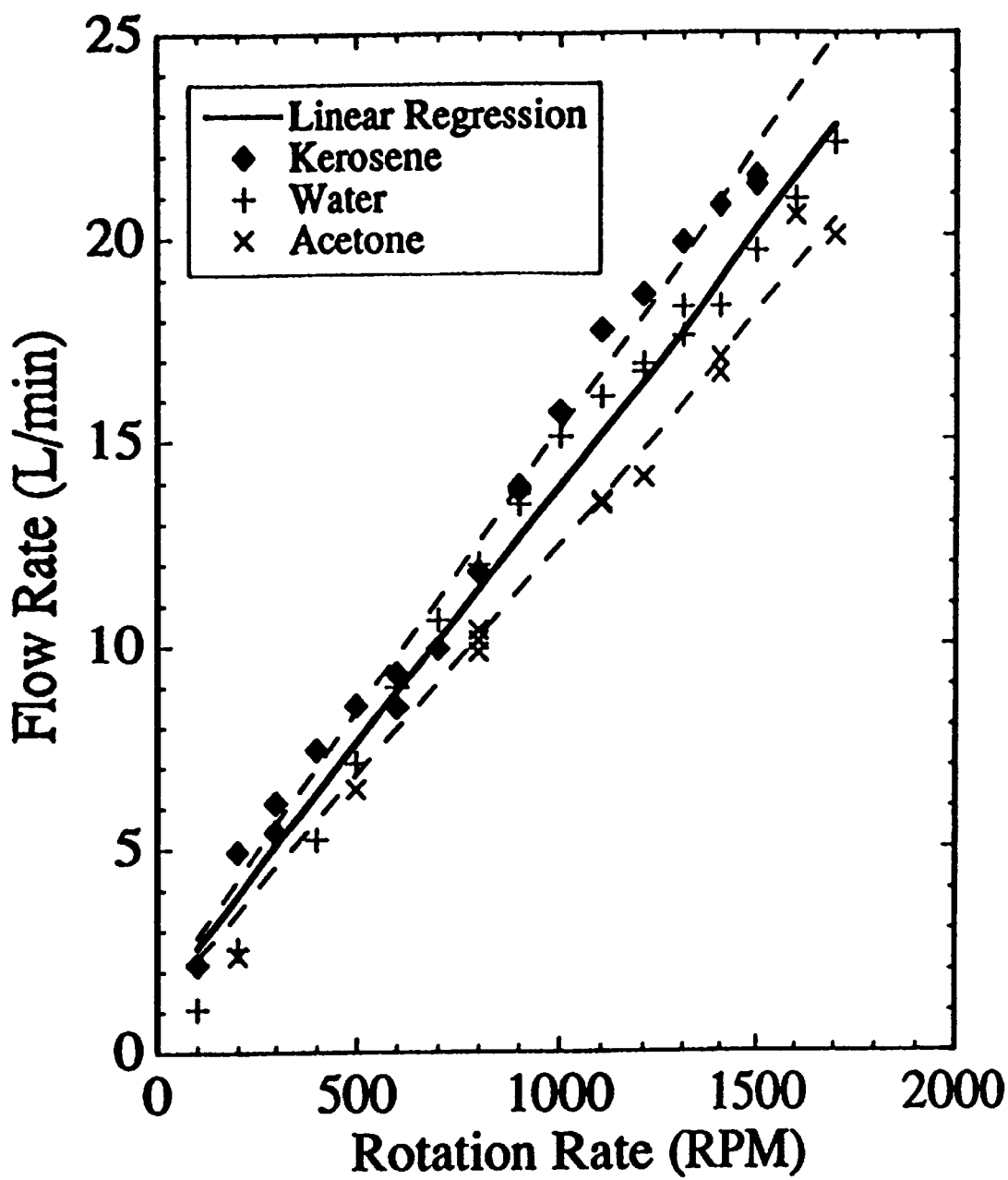
FIG. 2 is a chart with flow rate along the vertical axis and rotation rate along the horizontal axis illustrating flow calibration results of the high temperature fouling test unit of FIG. 1 for kerosene, water and acetone.

FIG. 2 illustrates the flow calibration results for kerosene, water, and acetone. Calibration tests were conducted at 3 to 5 atm. pressure, 50° C., and 65 to 230 kW/m$^2$ of power on the fouling probe 104. A linear relation between the rotation rate of the impeller 108 and the flow rate was observed, and the flow-calibration data fall within 10% of the linear regression. In both FIGS. 2 and 3, the dashed lines represent a 10% deviation from the linear regression.

The major elements of the heat transfer calibration are to determine the wall resistance, develop a predictive method for the heat transfer coefficient, and compare results with a conventional correlation for annular flow.

Figure 3:
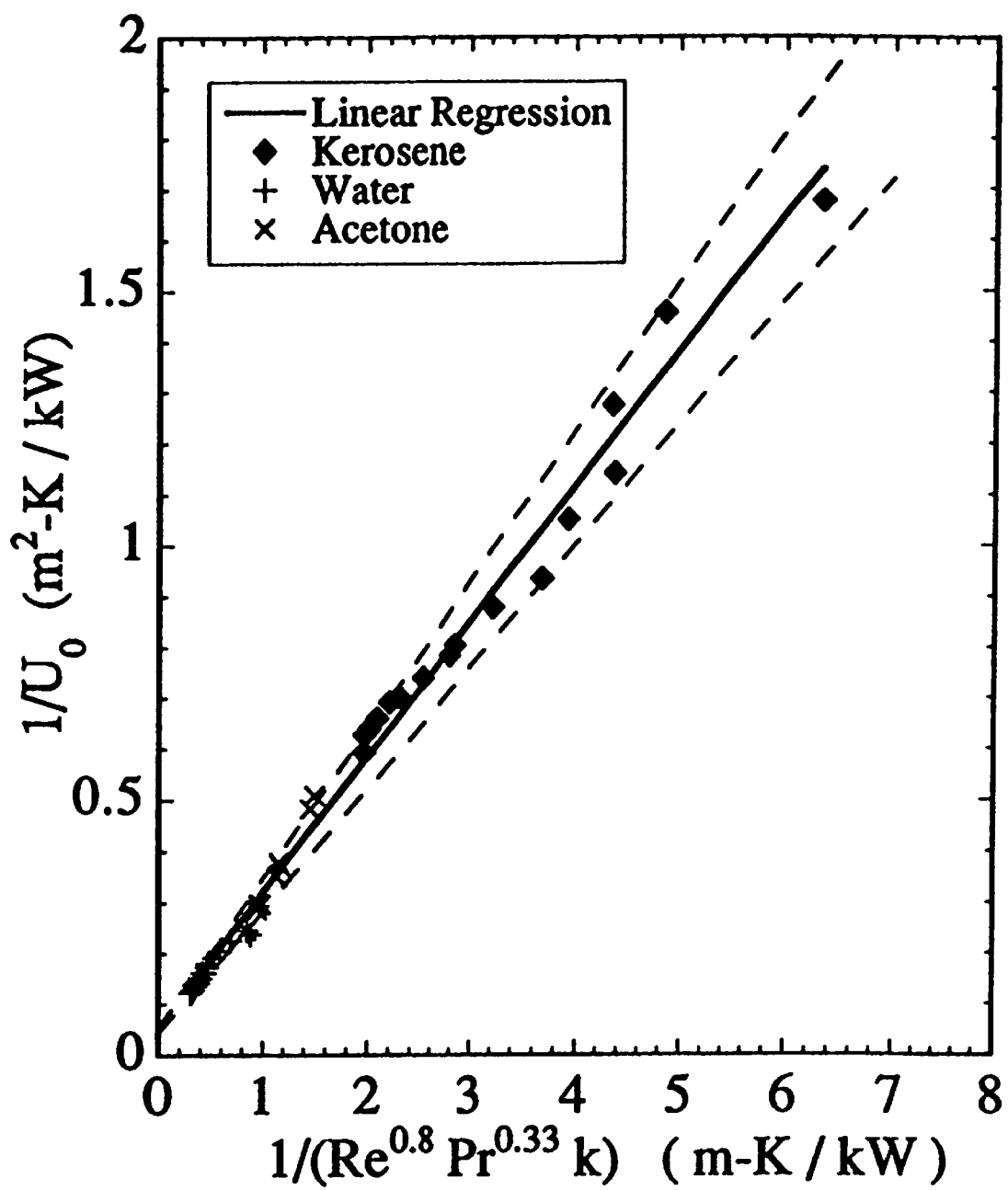
FIG. 3 is a chart illustrating a modified Wilson plot used to calculate the wall resistance of the high temperature fouling test unit of FIG. 1.

In FIG. 3, a modified Wilson plot is shown that is used in order to calculate the wall resistance. With this method, an appropriate ratio of the physical properties and the fluid velocity is used as an independent variable. Use of three test fluids with widely different physical properties increases the reliability of the calibration. A linear regression of the data gives an intercept of 0.052 m$^2$ K/kW for the wall resistance, $R_w$. This corresponds well within 10% of the theoretically calculated wall resistance of 0.056 m$^2$ K/kW. An important point, not considered by the previous investigators, is that the wall resistance changes during the fouling test as the wall temperature increases. As a result, the calculated fouling resistance is generally lower than the actual value. Therefore, changes in the thermal conductivity should be accounted for in calculating the fouling resistance.

Theoretical values of the heat transfer coefficient are calculated using the conventional correlation for annular flow. The constant in the conventional correlation is 0.02. Using this method, the experimental heat transfer coefficients are generally 30 to 50% greater than the theoretical values for the whole range of test conditions. Deviations of this magnitude are expected due to entrance effects for a low length-to-diameter ratio of 12. Therefore, a new value for the constant, equal to 0.03, was used to predict heat transfer coefficients in the fouling test unit 100, using correction factors to account for entrance effects.

Figure 4:
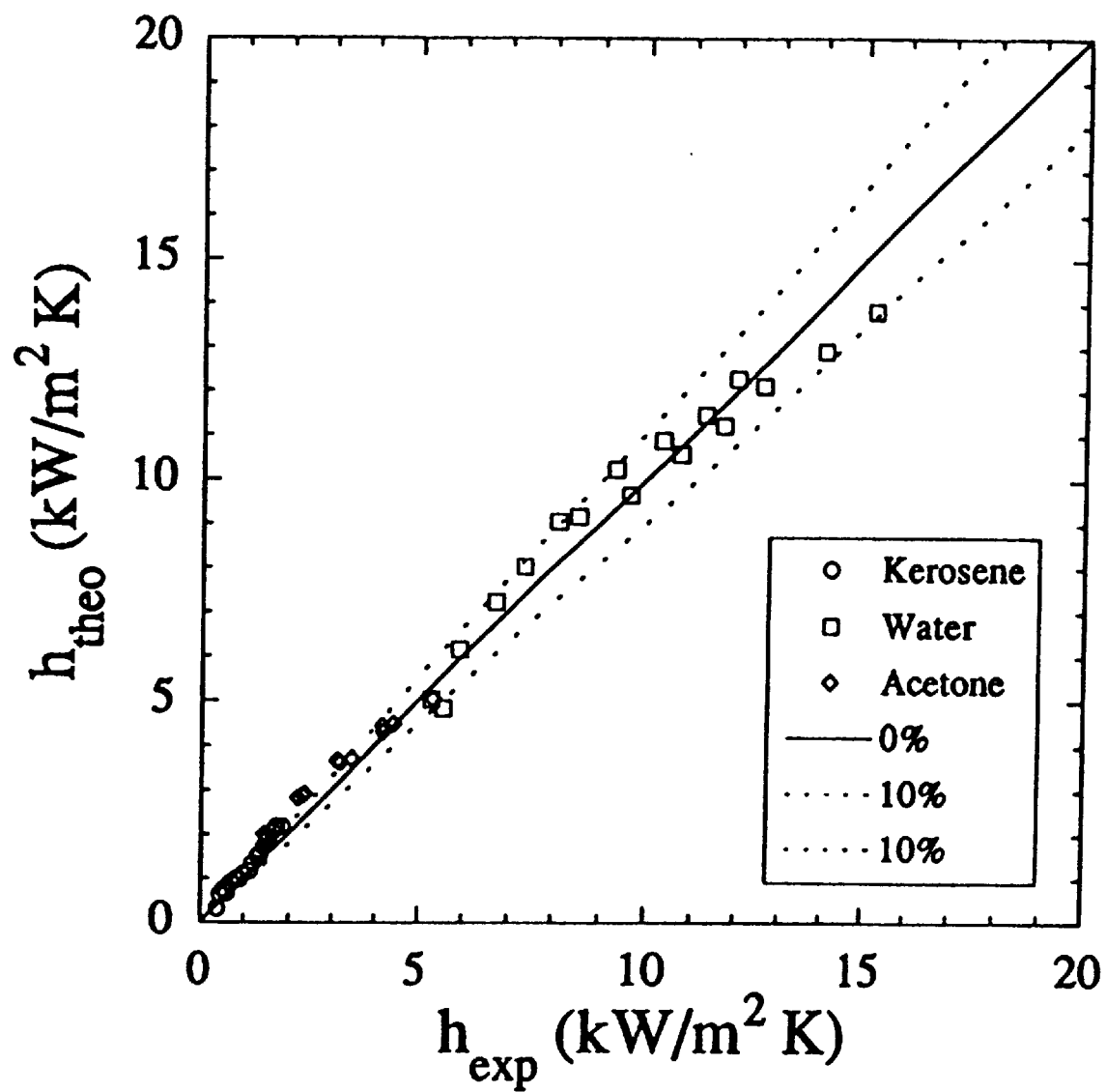
FIG. 4 is a chart illustrating theoretical and experimental heat transfer coefficients respectively along the vertical and horizontal axis of the high temperature fouling test unit of FIG. 1 for kerosene, water and acetone.

In FIG. 4, a comparison between the revised correlation and the experimental data is shown. Most of the data points lie within the measurement accuracy of 10%. The heat transfer results show that the fluid dynamics and thermal conditions are reproducible in the fouling unit 100 thereby qualifying it for fouling experiments.

The first set of experiments performed in the autoclave fouling test unit 100 are duplicates of those previously done in the organic-fluid fouling loops at Argonne and the University of British Columbia. Five liters of test fluid containing 10% Indene in Kerosene, prepared by weight and aerated for 4 hours under 4 atmospheres of pressure, is used for the fouling experiments described below.

Figure 5:
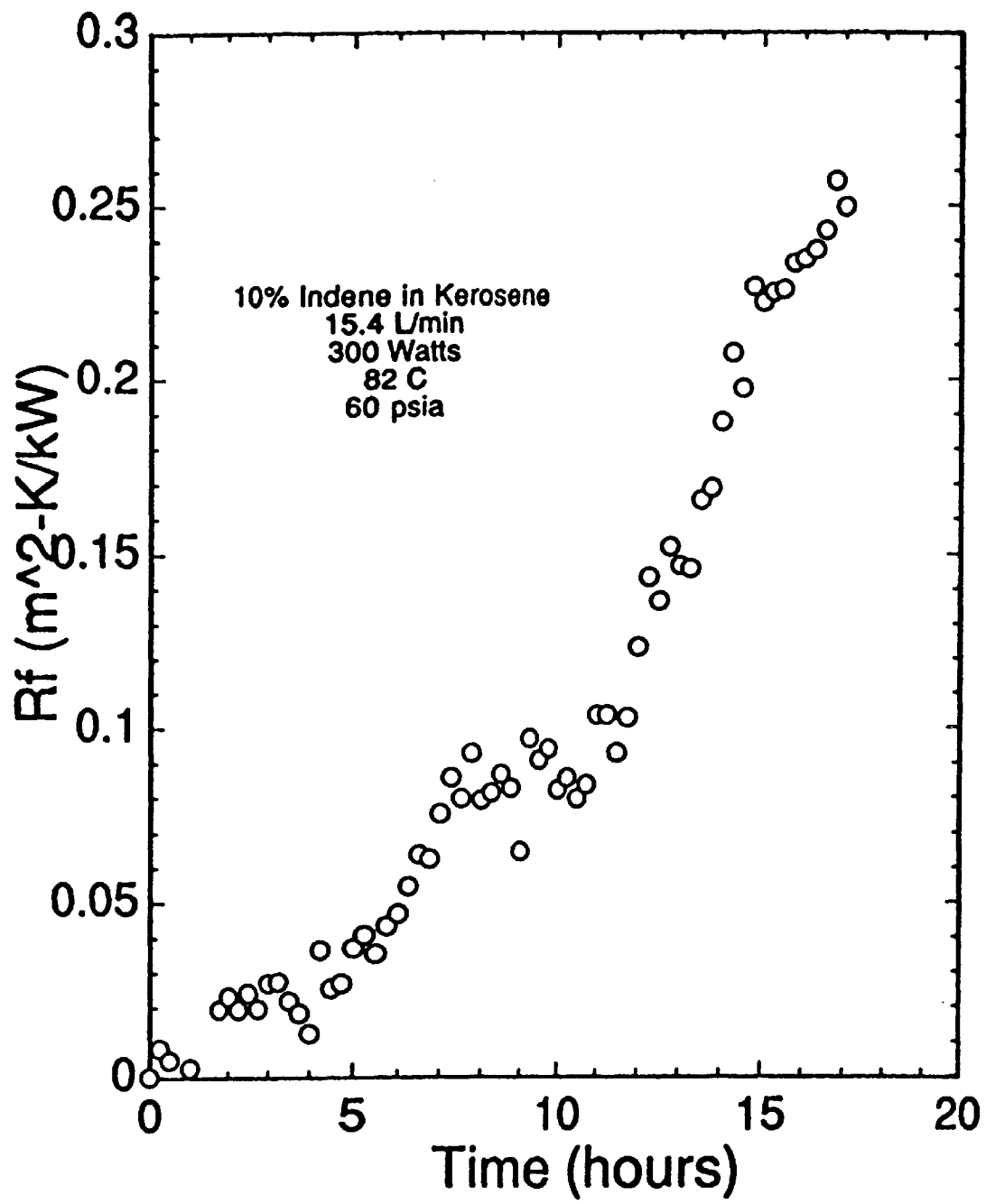
FIGS. 5, 6, and 7 are charts are charts with fouling resistance along the vertical axis and time in hours along the horizontal axis illustrating comparative, experimental operational results of the high temperature fouling test unit of FIG. 1.
Figure 6:
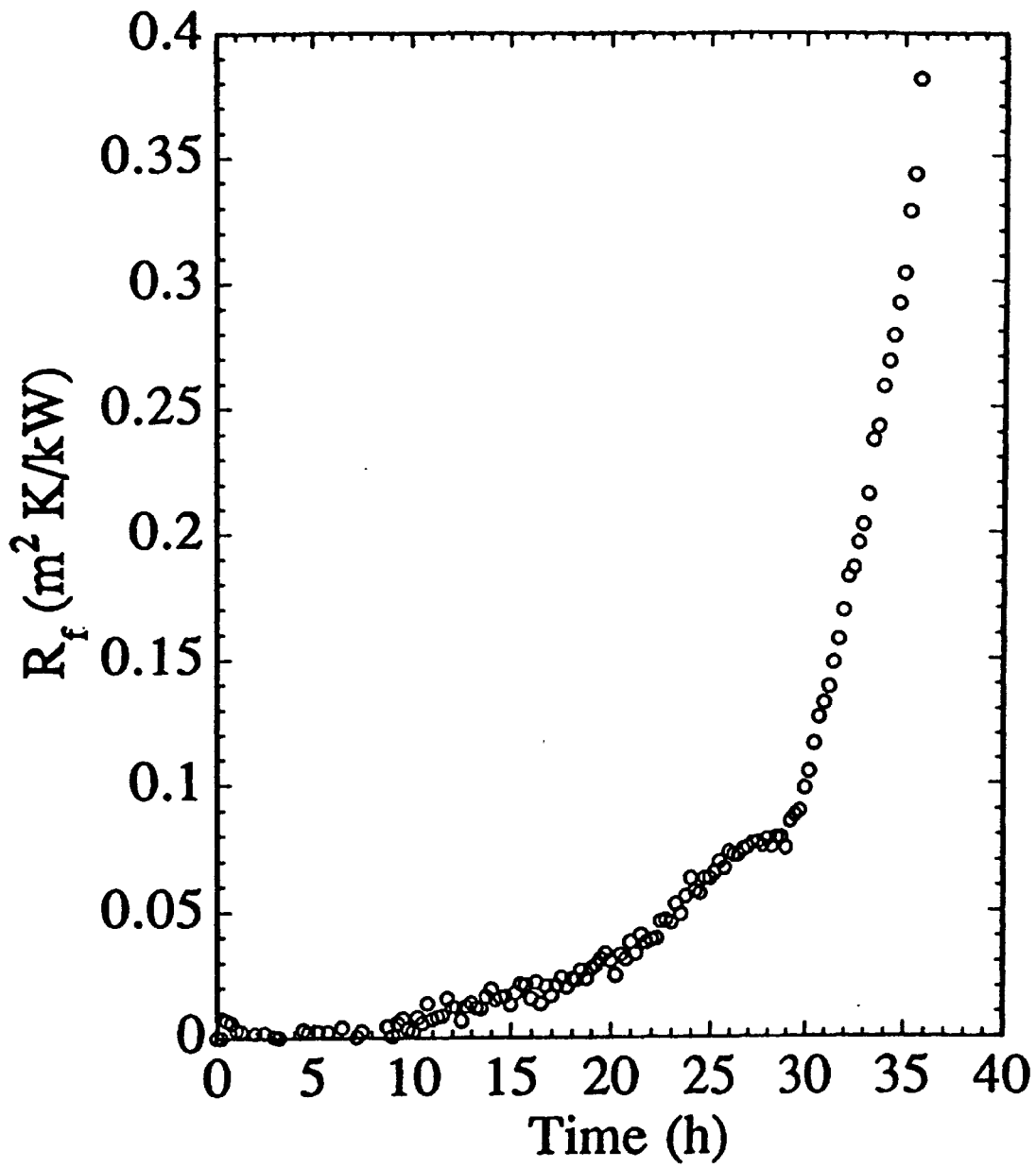
Figure 7:
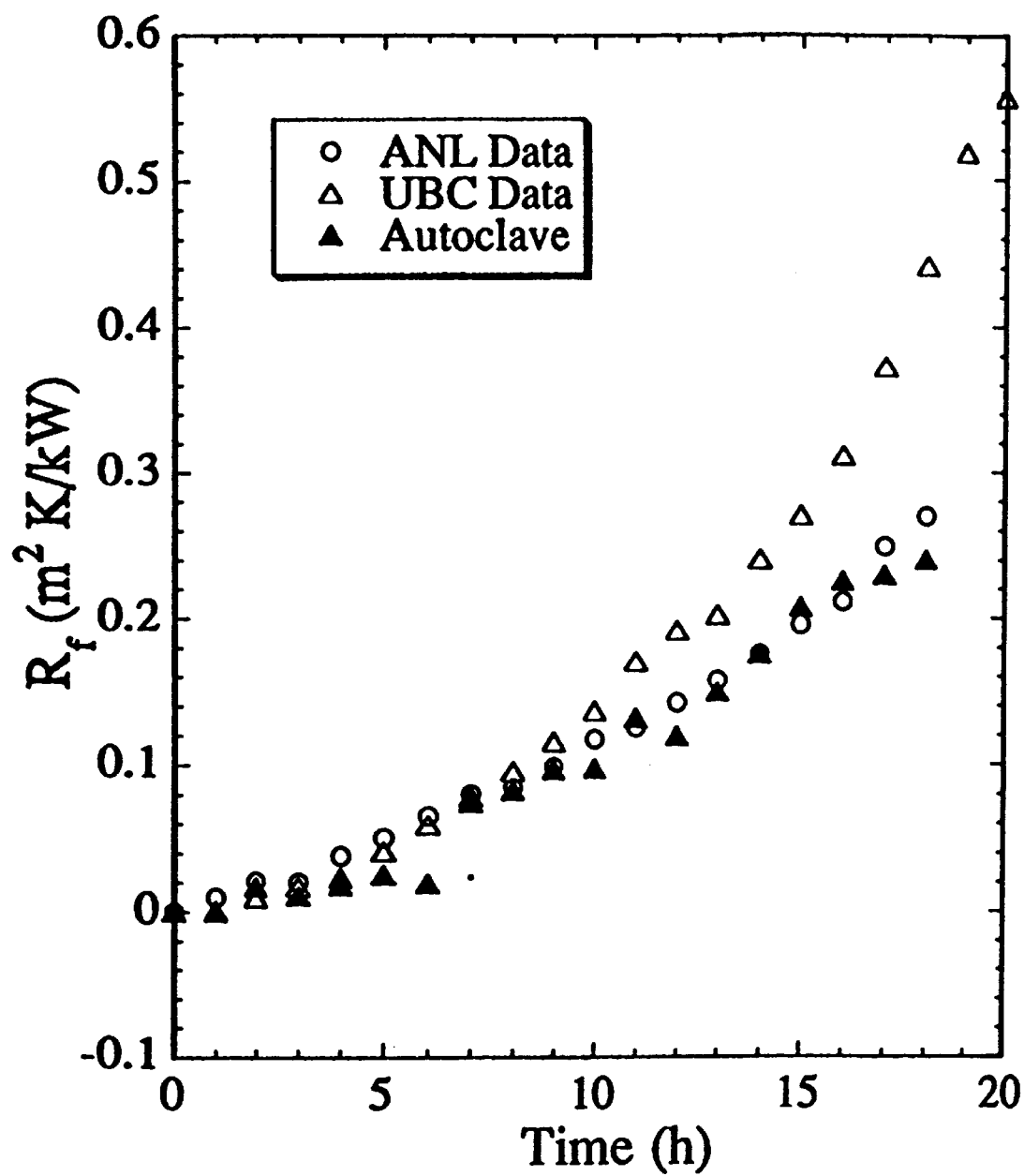

In FIGS. 5, 6, and 7, results from three of the indene/kerosene experimental runs are shown. These plots illustrate the increase in the fouling resistance typical of autoxidation of olefins shown by the previous experiments with flow loops. In FIG. 5, a fouling curve for 10% Indene in Kerosene with test conditions of a flow rate of 15.4 L/min, 300 Watts applied to the heating section 136, 82° C. and 60 psia. In FIG. 6, a fouling curve for 10% Indene in Kerosene with test conditions of a flow rate of 1 m/s, 194 kW/m$^2$ applied to the heating section 136, 82° C. and 4 atm. As seen in FIGS. 5 and 6, when the fluid Reynolds number through the annulus was increased from 6,100 to 10,400, the fouling rate dropped significantly. However, after an extended period of testing, an accelerated rate of fouling occurred due to build up of high concentrations of fouling precursor hydroperoxides.

A comparison between the data obtained using the fouling unit 100 and the earlier data with closed flow loops with in-tube and annular-flow units is shown in FIG. 7. In FIG. 7, the test conditions are a flow rate of 0.7 m/s, 214 KW/m² applied to the heating section 136, 82° C. and 4 atm. As shown in the following Table 1, the wall temperature, chemical composition, and the flow conditions were comparable for the three sets of data. The results show that the fouling curve obtained with the fouling test unit 100 is comparable to the other two sets of data. The results can be further validated by comparing the heat transfer coefficients from the three sets of experiments at the beginning before fouling started. On the basis of these comparisons, it can be concluded that the autoclave fouling test unit 100 produces heat transfer and fouling results comparable to the flow loop apparatus used in the previous investigations.

TABLE 1

Test conditions for indene/kerosene fouling experiments.

|  | Autoclave Unit | Argonne Flow Loop | UBC Annular-Flow Loop |
| --- | --- | --- | --- |
| Indene, wt % | 10 | 10 | 10 |
| Pressure, atm | 4 | 4 | 4 |
| Fluid T., ° C. | 82 | 82 | 84 |
| Surface T., ° C. | 188 | 188 | 188 |
| Reynolds number | 6,100 | 10,000 | 11,000 |
| Heat-Transfer Coefficient, m² K/kW. | 1.3 | 1.7 | 1.4 |

While the present invention has been described with reference to the details of the embodiments of the invention shown in the drawing, these details are not intended to limit the scope of the invention as claimed in the appended claims.

What is claimed is:

1. A fouling test unit comprising:
   an elongated flow tube;
   a fouling probe disposed within said flow tube, said fouling probe including a heated section;
   an annular passage defined between said fouling probe and said flow tube and extending from a fluid inlet to a fluid outlet, said passage adapted to have a fluid flow from said fluid inlet toward said fluid outlet;
   an impeller mounted within an enlarged section of said flow tube for inducing said fluid to flow within said annular passage from said fluid inlet toward said fluid outlet;
   a plurality of temperature responsive devices for monitoring a rate of heat transfer and a change in temperature of said fluid as said fluid flows through said annular passage, said plurality of temperature responsive devices including at least first and second temperature responsive devices disposed relative to said fouling probe for measuring the temperature of said fluid relative to said inlet and said fluid outlet; and
   a high pressure vessel enclosing said flow tube, said fouling probe and said impeller.

2. A fouling test unit as recited in claim 1 wherein said plurality of temperature responsive devices for monitoring said rate of heat transfer and said change in fluid temperature through said annular passage includes a plurality of thermocouples.

3. A fouling test unit as recited in claim 2 wherein at least some of said plurality of thermocouples are mounted on an interior surface of said flow tube adjacent said fouling probe.

4. A fouling test unit as recited in claim 2 wherein said plurality of thermocouples include at least one thermocouple mounted on said fouling probe.

5. A fouling test unit as recited in claim 1 wherein said plurality of temperature responsive devices for monitoring said rate of heat transfer and said change in fluid temperature through said annular passage includes a differential resistance temperature device installed across said flow tube for monitoring said change in fluid temperature through said annular passage.

6. A fouling test unit as recited in claim 5 wherein said differential resistance temperature device monitors said change in fluid temperature through said annular passage from a first point near said fluid inlet of said annular passage to a second point near said fluid outlet of said annular passage.

7. A fouling test unit as recited in claim 1 wherein said flow tube is vertically mounted within said vessel and wherein said enlarged section of said flow tube with said impeller mounted therein is within an upper part of said flow tube.

8. A fouling test unit as recited in claim 7 wherein said upper part of said flow tube includes an enlarged cylindrical portion extending above said fouling probe and containing said impeller.

9. A fouling test unit comprising:
   a vertically disposed, elongated flow tube;
   a fouling probe disposed within said flow tube, said fouling probe including a heated section;
   an annular passage defined between said fouling probe and said flow tube and extending from a fluid inlet to a fluid outlet, said passage adapted to have a fluid flow from said fluid inlet toward said fluid outlet;
   an impeller mounted within an upper, enlarged part of said flow tube for inducing said fluid to flow upwardly within said annular passage from said fluid inlet toward said fluid outlet;
   a plurality of temperature responsive devices for monitoring a rate of heat transfer and a change in temperature of said fluid as said fluid flows through said annular passage, said plurality of temperature responsive devices including at least first and second temperature responsive devices disposed relative to said fouling probe for measuring the temperature of said fluid relative to said inlet and said fluid outlet; and
   a high pressure vessel enclosing said flow tube, said fouling probe and said impeller.

10. A fouling test unit as recited in claim 9 wherein said plurality of temperature responsive devices for monitoring said rate of heat transfer and said change in fluid temperature through said annular passage includes a plurality of thermocouples.

11. A fouling test unit as recited in claim 10 wherein said plurality of thermocouples include at least one thermocouple mounted on said heated section of said fouling probe.

12. A fouling test unit as recited in claim 10 wherein said plurality of thermocouples include at least one thermocouple mounted on an upper portion of said fouling probe.

13. A fouling test unit as recited in claim 10 wherein said plurality of thermocouples include at least one thermocouple mounted on a lower portion of said fouling probe.

14. A fouling test unit as recited in claim 9 wherein said plurality of temperature responsive devices for monitoring said rate of heat transfer and said change in fluid temperature through said annular passage includes a differential resistance temperature device installed across said flow tube for monitoring said change in fluid temperature through said annular passage from a first point near said fluid inlet at a lower end of said flow tube to a second point near said fluid outlet at an upper end of said fouling probe.

* * * * *